(12) United States Patent
Jiang et al.

(10) Patent No.: US 11,377,398 B2
(45) Date of Patent: Jul. 5, 2022

(54) ETHYLENE SELECTIVE OLIGOMERIZATION CATALYST SYSTEMS AND METHOD FOR ETHYLENE OLIGOMERIZATION USING THE SAME

(71) Applicant: Tianjin University of Science & Technology, Tianjin (CN)

(72) Inventors: Tao Jiang, Tianjin (CN); Yanhui Chen, Tianjin (CN); Le Zhang, Tianjin (CN); Fakhre Alam, Tianjin (CN); Huaiqi Shao, Tianjin (CN); Jian Li, Tianjin (CN); Bing Yan, Tianjin (CN)

( * ) Notice: Subject to any disclaimer, the term of this patent is extended or adjusted under 35 U.S.C. 154(b) by 0 days.

(21) Appl. No.: 16/215,550

(22) Filed: Dec. 10, 2018

(65) Prior Publication Data
US 2019/0106366 A1    Apr. 11, 2019

Related U.S. Application Data

(63) Continuation of application No. PCT/CN2017/115496, filed on Dec. 11, 2017.

(51) Int. Cl.
| | | |
|---|---|---|
| C07C 2/36 | (2006.01) |
| B01J 31/02 | (2006.01) |
| B01J 27/132 | (2006.01) |
| B01J 31/14 | (2006.01) |
| B01J 31/24 | (2006.01) |
| B01J 31/22 | (2006.01) |
| B01J 31/16 | (2006.01) |

(52) U.S. Cl.
CPC .............. *C07C 2/36* (2013.01); *B01J 27/132* (2013.01); *B01J 31/0267* (2013.01); *B01J 31/143* (2013.01); *B01J 31/1608* (2013.01); *B01J 31/2273* (2013.01); *B01J 31/2404* (2013.01); *B01J 2231/20* (2013.01); *B01J 2531/0244* (2013.01); *B01J 2531/0258* (2013.01); *B01J 2531/62* (2013.01); *C07C 2527/132* (2013.01); *C07C 2531/02* (2013.01); *C07C 2531/14* (2013.01); *C07C 2531/24* (2013.01)

(58) Field of Classification Search
None
See application file for complete search history.

(56) References Cited

U.S. PATENT DOCUMENTS

| | | |
|---|---|---|
| 3,635,937 A | 1/1972 | Bauer et al. |
| 3,676,523 A | 7/1972 | Mason |
| 3,906,053 A | 9/1975 | Lanier |
| 6,184,428 B1 | 2/2001 | Zahoor et al. |
| 2011/0160412 A1* | 6/2011 | Thieuleux ............ B01J 31/0295 526/126 |

FOREIGN PATENT DOCUMENTS

| | | | |
|---|---|---|---|
| CN | 102007136 A | 4/2011 | |
| CN | 104803818 A | 7/2015 | |
| DE | 1443927 | 12/1968 | |
| EP | 0611743 A2 | 8/1994 | |
| KR | 10-2016-0064840 | * 6/2016 | .............. C07C 2/08 |
| WO | 99/02472 | 1/1999 | |
| WO | 2008004986 A1 | 1/2008 | |

OTHER PUBLICATIONS

Kim et al. to KR 10-2016-0064840, a machine translation (Year: 2016).*
Novel olefin polymerization catalysts based on iron and cobal, Jan. 1, 1998, George J. P. Britovsek ; Vernon C. Gibson ; Brian S. Kimberley ; Peter J. Maddox ; Stuart J. McTavish; Gregory A. Solan;Andrew J. P. White; and David J. Williams.
Iron-Based Catalysts with Exceptionally High Activities and Selectivities for Oligomerization of Ethylene to Linear r-Olefins, Jul. 7, 1998, Brooke L. Small; Maurice Brookhart.

* cited by examiner

*Primary Examiner* — Yun Qian
(74) *Attorney, Agent, or Firm* — Bayramoglu Law Offices LLC

(57) ABSTRACT

The disclosure provides a catalyst system and a method for ethylene oligomerization using this. The catalyst system contains: ligand a, containing carbene groups of imidazole ring type; transition metal compound b, that is one of IVB~VIII group metal compounds; activator c, that is a compound containing III A group metals; the ligand a contains at least one group as shown in general formula I:

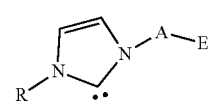

in which, bridging group A contains a main chain including alkyl, alkenyl, aryl groups or the combination of them and the first heteratom; E is a linear or cyclic group containing the second heteroatom; R is a hydrocarbyl group. The catalyst system is especially used for trimerization and tetramerization of ethylene. The catalyst system has high selectivity for 1-hexene and 1-octene, low selectivity for 1-butene and 1-$C_{10+}$, and the total percent content of $C_6$~$C_8$ linear □α-olefin in the product is more than 90% by mass.

5 Claims, No Drawings

ETHYLENE SELECTIVE OLIGOMERIZATION CATALYST SYSTEMS AND METHOD FOR ETHYLENE OLIGOMERIZATION USING THE SAME

TECHNICAL FIELD

The present invention relates to a catalyst system for selective oligomerization of ethylene and a method of ethylene oligomerization using the same.

BACKGROUND

Linear alpha-olefins are a kind of important organic chemical raw materials. They are widely used in co-/polymerization with ethylene to produce polyethylene, surfactants, lubricants and oil additives. The light components (C4-C8) can be used as co-monomers for copolymerization of ethylene to produce linear low-density polyethylene (LLDPE). Especially, high purity 1-hexene and 1-octene can significantly improve the abrasion resistance and other chemical/mechanical properties of LLDPE.

With the continuous development of the global economy, the demand for high performance polyethylene is increasing, and the demand for 1-hexene and 1-octene continues to grow at an average annual rate of more than 5.4%. The main methods for industrial production of 1-hexene and 1-octene are paraffin cracking, ethylene oligomerization and extraction-separation. Among them, ethylene oligomerization is the main method for the production of 1-hexene and 1-octene. For example, U.S. Pat. No. 6,184,428 disclosed a nickel catalyst, using boron compounds as co-catalysts, can catalyze ethylene oligomerization to obtain linear a-olefin mixtures, in which 1-hexene content accounted for 22%, 1-octene content accounted for 19%. In SHOP process (U.S. Pat. Nos. 3,676,523, 3,635,937), the contents of 1-hexene and 1-octene in the ethylene oligomerization products were 21% and 11%, respectively. The contents of 1-hexene and 1-octene in Gulfs Chevron process (DE1443927) and Ethyl's process (BP/Amoco, U.S. Pat. No. 3,906,053) are generally low to 13-25%. In addition, the iron-based catalysts reported by Brookhart et al (J. Am. Chem. Soc., 1998, 120:7143; Chem. Commun. 1998, 849; WO 99/02472) were used for ethylene oligomerization, and the contents of 1-hexene and 1-octene were also lower than 20%. In the existing processes, the contents of 1-hexene and 1-octene in oligomerization products are impossible to be high enough. If we want to get the highly pure 1-hexene and 1-octene, we need to separate them by multi-tower distillation, which is complex and huge for the equipment investment.

Therefore, the design of a highly selective ethylene oligomerization catalyst system and the use thereof for the production of 1-hexene and 1-octene, with high contents of 1-hexene and 1-octene, deserves the attention of the industry.

SUMMARY OF THE INVENTION

One aspect of the present invention aims to present a catalyst system and the use thereof for selective oligomerization of ethylene with high catalytic activity and high selectivity, to solve the technical problems of low catalytic activity and low total selectivity of 1-hexene and 1-octene in the catalyst system.

The technical proposal of the invention is as follows:
a catalyst system for selective oligomerization of ethylene comprising three components:
a ligand (a), containing carbene groups of imidazole ring type;
a transition metal compound (b), that is one of IVB~VIII group metal compounds;
an activator (c), that is a compound containing III A group metals.

The ligand (a) contains at least one group as shown in general formula I as shown below:

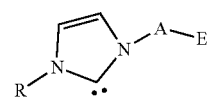

I in which, bridging group A contains a main chain including alkyl, alkenyl, aryl groups or the combination of them and a first heteroatom.

E is a linear or cyclic group containing a second heteroatom.

R is a hydrocarbyl group.

Further, the first heteroatom is one of the atoms such as silicon, tin, boron, phosphorus, nitrogen, oxygen and sulfur.

Further, the bridging group A is —(CH$_2$)$_n$—(1≤n≤8), phenyl, biphenyl, naphthyl, anthracene or —(CH$_2$)$_n$—SiR'R"—(CH$_2$)$_m$(0≤n≤3, 0≤m≤3), in which R' and R" are independently selected from methyl, isopropyl, cyclohexanyl, cyclopentyl, phenyl, naphthalene or 2,6-diisopropyl phenyl, respectively.

Further, the second heteroatom is one of the atoms such as phosphorus, nitrogen, sulfur and oxygen.

Further, E as shown in the general formula I contains alkyl phosphino, aryl phosphino, alkyl-aryl phosphino, alkyl amino, aryl amino, mercapto, and preferably diisopropyl phosphino, dicyclohexyl phosphino, dimethyl phosphino, diethyl phosphino, diphenyl phosphino, di-o-methyl phenyl phosphino, di-o-ethyl phenyl phosphino, di-isopropyl Phenyl phosphino, diphenyl phosphino, dinaphthyl phosphino, dimethylamino, diethylamino, diisopropylamino, diphenylamino, dinaphthyl amino, methoxy, ethoxy, phenoxy, isopropoxy, methyl mercapto, ethyl mercapto, phenylmercapto, isopropylmercapto.

Further, R as shown in the general formula I is selected from alkyl, alkenyl or aromatic groups and their derivatives, preferably methyl, isopropyl, cyclopentyl, cyclohexyl, phenyl, o-methylphenyl, o-ethylphenyl, o-isopropylphenyl, 2,4-dimethylphenyl, 2,4-diethylphenyl, 2,4-diisopropylphenyl, 2,4-dibutylphenyl, 2,6-dibutylphenyl. Diisopropylphenyl, 2,6-dimethylphenyl, 2,6-diethylphenyl, 2,6-dibutylphenyl, 2,4,6-trimethylphenyl, 2,4,6-triethylphenyl, 2,4,6-triisopropylphenyl, naphthyl, anthryl, biphenyl.

Further, the activator (c) is one or more selected from an alkyl aluminum compound, an alkyl aluminoxane compound, an organic boron compound, an organic salt, an inorganic acid or an inorganic salt; the alkyl aluminoxane compound includes an alkyl aluminoxane compound free of volatile components.

Further, the activator (c) is a mixture of an alkyl aluminum compound and an alkyl aluminoxane compound removed of volatile components, in which the alkyl aluminum compound is a triethyl aluminum (TEAL), and the alkyl aluminoxane compound is a methyl aluminoxane (DMAO) removed of volatile components; the molar ratio of the TEAL to DMAO is 0.01~100, preferably 0.1~10.

Furthermore, the molar ratio of the ligand (a), transition metal compound (b) and activator (c) is 1:(0.5~100):(0.1~5000).

The invention also disclosure an ethylene oligomerization reaction method, including the ethylene oligomerization reaction carried out in the presence of the above catalyst system.

Further, the reaction was carried out in an inert solvent, which is one or more selected from alkanes, aromatic hydrocarbons, olefins, and ionic liquids.

Further, the reaction temperature is 0~200° C.

Further, the reaction pressure is 0.1 MPa~50 MPa.

Relative to exiting technology, the catalyst system for ethylene selective oligomerization of the present invention has the following advantages:

(1) The ethylene selective oligomerization catalyst system of the present invention is used for ethylene oligomerization, especially for ethylene trimerization and tetramerization. The catalyst system has high activity, high total selectivity of the target product 1-hexene and 1-octene, low mass percent content of 1-butene and 1-$C_{10+}$, and the mass percent content of $C_6$-$C_8$ linear α-olefin in the products is more than 90%.

(2) The ethylene selective oligomerization catalytic system of the invention is used for ethylene oligomerization. The total selectivity toward 1-hexene and 1-octene is high, and, in the two components of 1-hexene and 1-octene, the selectivity of one is obviously higher than the other one. High purity 1-hexene or 1-octene can be obtained by simple separation.

(3) The synthesis of this catalyst system is simple and less cost. The catalyst also has a long life.

DETAILED DESCRIPTION

The present invention will be described in detail with examples.

A catalyst system for selective oligomerization of ethylene comprises three components:

a ligand (a), containing carbene groups of imidazole ring style;

a transition metal compound (b), that is one of IVB~VIII group metal compounds;

an activator (c), that is a compound containing III A group metals;

the ligand (a) contains at least one group as shown in general formula I as shown below:

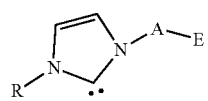

I in which, bridging group A contains a main chain including alkyl, alkenyl, aryl groups or the combination of them and a first heteratom.

E is a linear or cyclic group containing a second heteroatom.

R is a hydrocarbyl group.

The embodiment of the present invention provides a catalyst system for selective oligomerization of ethylene, comprising three components: ligand (a), transition metal compound (b) and activator (c). The ligand (a) contains at least one group as shown in general formula I, which is a ligand contains carbene group of imidazole ring type; the transition metal compound (b) is a metal compound of the IVB~VIII group as the central metal atom; the activator (c) is a compound containing the IIIA group metals, which mainly plays an active role.

There is significant effect of the ligand's structure on the activity and the selectivity of 1-hexene and 1-octene for selective oligomerization of ethylene. In the existing technology of ethylene selective tetramerization, P atom in the ligand's structure is mostly used as the donor atom, coordinating with metal center to catalyze ethylene selective oligomerization, especially ethylene tetramerization. However, due to the unstable structure of phosphine ligands, it is easy to decompose at high temperature and under the action with alkyl aluminum and alkyl aluminoxane, resulting in the mutation of catalyst or deactivation. So, it is always difficult to reach a higher level on the activity and selectivity of ethylene selective tetramerization. While the carbene ligands of imidazole ring type of the present embodiment are easy to synthesize, less toxic, stable in structure, easy to control in space resistance and electronic effect, similar coordination ability to that of P atom.

For the activator of the catalyst system provided by the embodiment of the invention, when the catalyst system catalyzes ethylene oligomerization, appropriate metal compound of IIIA group is selected to achieve the best activation effect, according to the different alkylation intensity.

For the transition metal compounds of the catalyst system provided by the embodiment of the invention, the metal compounds of IVB~VIII group are selected.

In the catalyst system provided by the embodiment of the invention, the ligand structure, combining the corresponding transition metal compounds and activators, has an important influence on the catalytic activity and the selectivity of 1-hexene and 1-octene for ethylene selective oligomerization. The stable coordination of carbene group can maintain the coexistence with the activators such as alkyl aluminum and alkyl aluminoxane for a long term and influence the metal centre by steric-hinerance and electronic effects and further the catalytic activity and selectivity of the catalyst, resulting to excellent total selectivity of 1-hexene and 1-octene for ethylene selective oligomerization of the catalyst system of the invention.

In an embodiment of the invention, the molar ratio of ligand (a) to transition metal compound (b) in the catalyst system can be 1:(0.5~100).

In another embodiment of the invention, the molar ratio of ligand (a) to activator (c) in the catalyst system can be 1:(0.1-5000), preferably 1:(1-1000), and more preferably 1:(1-200).

Specifically, the molar ratio of ligand (a), transition metal compound (b) and activator (c) can be 1:(0.5-100):(0.1-5000), preferably 1:(0.5-100):(0.1-1000), and more preferably 1:(0.5-100):(0.1-200).

The three components of the catalyst system are further explained below.

(1) Ligand (a)

In an embodiment of the present invention, the main chain of bridging group A includes chain-like groups containing carbon atoms, such as methane, ethane, propane, butane, pentane, hexane, heptane and octane. Preferably, bridging group A can be —$(CH_2)_n$— (1≤n≤8).

In another embodiment of the invention, the main chain of the bridging group A may comprise phenyl, biphenyl, naphthyl, anthrayl and their derivatives.

In another embodiment of the invention, the main chain of the bridged group A includes aromatic hydrocarbons, olefin groups and their derivatives, such as methylphenyl.

In another embodiment of the invention, the main chain of the bridging group A includes a second heteroatom, which is the one of atoms such as silicon, tin, boron, phosphorus, nitrogen, oxygen and sulfur, and a chain-like group.

Preferably, the bridging group A can be —$(CH_2)_n$—SiR'R"—$(CH_2)_m$ (0≤n≤3, 0≤m≤3), in which R' and R" are independently selected from methyl, isopropyl, cyclohexanyl, cyclopentyl, phenyl, naphthyl or 2,6-diisopropyl phenyl, respectively.

In one embodiment of the invention, E is a chain or ring group containing a second heteroatom, which is one of the atoms such as phosphorus, nitrogen, sulfur and oxygen.

Preferably, E contains alkyl phosphino, aryl phosphino, alkyl aryl phosphino, alkyl amino, aryl amino, mercapto.

Preferably, E contains diisopropyl phosphino, dicyclohexyl phosphino, dimethyl phosphino, diethyl phosphino, diphenyl phosphino, di-o-methyl phenyl phosphino, di-o-ethyl phenyl phosphino, di-o-isopropyl phenyl phosphino, di-diphenyl phosphino, di-naphthalene phosphino, dimethyl amino, diethyl amino, di-isopropyl amino, di-di-isopropyl amino, di-phenyl amino, dinaphthyl amino, methoxy, ethoxy, phenoxy, isopropoxy, methyl mercapto, ethyl mercapto, phenylmercapto, isopropyl mercapto and so on.

Preferably, E contains diphenyl phosphino, diphenyl amino and ethyl mercapto.

In one embodiment of the invention, R is a hydrocarbyl group.

Preferably, R can be alkyl and aromatic groups.

Preferably, R can be selected from methyl, isopropyl and unsaturated hydrocarbyl groups.

Preferably, R can also be selected from cycloalkyl and aryl groups.

Preferably, R may be selected from cyclopentyl, cyclohexyl, phenyl, o-methylphenyl, o-ethylphenyl, o-isopropylphenyl, 2,4-dimethylphenyl, 2,4-diethylphenyl, 2,4-diisopropylphenyl, 2,4-dibutylphenyl, 2,6-diisopropylphenyl, 2,6-dimethylphenyl, 2,6-diethylphenyl, 2,6-dibutylphenyl, 2,6-dibutylphenyl. 4,6-trimethylphenyl, 2,4,6-triethylphenyl, 2,4,6-triisopropylphenyl, naphthyl, anthryl, biphenyl, etc.

Suitable ligand (a) may contain one or more units, whose structure is shown in general formula I, hanging together by groups, chemical bonds or intermolecular forces to give bridged, dendritic and star-shaped compounds. It may also be a polymeric compound formed by binding to a polymer chain.

Preferably, the ligand (a) can be $C_3H_2N_2R$-A-E, in which A, E and R are as mentioned above.

Preferably, the ligand (a) can also be $[C_3H_2N_2R-A-E]_nC$ (n≥2), in which A, E and R are as mentioned above.

(2) Transition Metal Compound (b)

In an embodiment of the invention, the transition metal compound (b) contains one of the metals such as chromium, molybdenum, tungsten, lead, cobalt, titanium, tantalum, vanadium, zirconium, iron, nickel and palladium.

Preferably, the transition metal compound (b) is one of the compounds such as $CrCl_3(THF)_3$, $CoCl_3$, $PbCl_2(COD)$, $Pb(Ac)_2$.

Preferably, the transition metal compound (b) is a transition metal compound containing chromium, zirconium or titanium.

More preferably, the transition metal compound (b) is a transition metal compound containing chromium. Suitable chromium compounds can be displayed by the general formula $CrR''_m$, in which R" is an organic negative ion or a neutral molecule, R" usually contains 1~10 carbon atoms, n is an integer of 0~6, and the valence state of chromium is 0~6. The specific R" group is organic compound or group containing carboxyl, β-diketone or hydrocarbyl. Considering the solubility and maneuverability, the more suitable chromium compounds include chromium acetate, chromium isooctanoate, chromium octanoate, chromium acetylacetone, chromium diisoprene, chromium diphenyl, $CrCl_3(THF)_3$, $CrCl_2(THF)_2$, (phenyl) tricarbonyl chromium and hexacarbonyl chromium.

(3) Activator (c)

In an embodiment of the present invention, the activators (c) is alkyl aluminum compounds, alkyl aluminoxane compounds, organic boron compounds, organic salts, inorganic acids, inorganic salts or their mixture, in which the alkyl aluminoxane compounds include the aluminoxanes removed volatile components.

Specifically, alkyl aluminum compounds can be various trialkyl aluminum, such as TEAL, triisobutyl aluminum, tri-n-butyl aluminum, tri-n-hexyl aluminum or tri-n-octyl aluminum; alkyl aluminum compounds can also be alkyl aluminum halides, alkyl aluminum hydrides or alkyl aluminum hemichlorides, such as $AlEt_2Cl$ and $Al_2Et_3Cl_3$; alkyl aluminoxane compounds can be selected from methyl aluminoxane, ethyl aluminoxane, isobutyl aluminoxane and modified aluminoxane, such as modified methyl aluminoxane (MMAO) and so on.

Specifically, the activator c is a mixture of an alkyl aluminum compound and an aluminoxane removed volatile components, in which the alkyl aluminum compound is TEAL and the alkyl aluminoxane compound is DMAO.

Preferably, the molar ratio of TEAL to DMAO is 0.01~100, preferably 0.1~10.

In another embodiment of the invention, the activators of organic salt are methyl lithium, methyl magnesium bromide, etc.; the activators of inorganic acid and inorganic salt are tetrafluoroborate ether, tetrafluoroborate, hexafluoroantimonate, etc.; the organic boron compounds include cycloboroxane, sodium borohydride, triethylborane, trifluorophenyl boron, tributyl borates and so on.

According to the above, in an embodiment of the present invention, the bridging group A of ligand (a), in an appropriate catalyst system, may have the general formula —$(CH_2)_n$—(1≤n≤8) or contain the linking groups of phenyl, biphenyl, naphthyl, anthryl and their derivatives in the main chain, or include the straight-chain linking group —$(CH_2)_n$—SiR'R"—$(CH_2)_m$ (0≤n≤3, 0≤m≤3) in the main chain containing silicon atoms. R' and R" are each independently methyl, isopropyl, cyclohexyl, cyclopentyl, phenyl, naphthyl, 2,6-diisopropyl phenyl. R is methyl, isopropyl, cyclopentyl, cyclohexyl, phenyl, o-methylphenyl, o-ethylphenyl, o-isopropylphenyl, 2,4-dimethylphenyl, 2,4-diethylphenyl, 2,4-diisopropylphenyl, 2,4-dibutylphenyl, 2,6-diisopropylphenyl, 2,6-dimethylphenyl, 2,6-diethylphenyl, 2,6-dibutylphenyl, 2,4,6-trimethylphenyl, 2,4,6-triethylphenyl, 2,4,6-triisopropylphenyl, naphthyl, anthryl, biphenyl. E is selected from diisopropyl phosphino, dicyclohexyl phosphino, dimethyl phosphino, diethyl phosphino, diphenyl phosphino, di-o-methyl phenyl phosphino, di-o-isopropyl phenyl phosphino, di-phenyl phosphino, di-naphthyl phosphino, dimethyl amino, diethyl amino, di-isopropyl amino, diphenyl amino dinaphthylamino, methoxy, ethoxy, phenoxy, isopropoxy, methyl mercapto, ethyl mercapto, phenylmercapto, isopropyl mercapto, etc.

The transition metal compound (b) is $CrCl_3(THF)_3$, $CoCl_3$, $PbCl_2(COD)$, $Pb(Ac)_2$ and is also each chromium acetate, chromium isooctanate, chromium octanoate, chromium acetylacetone, chromium diisoprene, chromium diphenyl, $CrCl_3(THF)_3$, $CrCl_2(THF)_2$. (phenyl) three carbonyl chromium and six carbonyl chromium.

Activator (b) is trialkyl aluminum compounds, such as triethyl aluminum, triisobutyl aluminum, tri-n-butyl aluminum, tri-n-hexyl aluminum and tri-n-octyl aluminum, alkyl aluminum halides, alkyl aluminum hydrides or alkyl aluminum hemichlorides, such as $AlEt_2Cl$ and $Al_2Et_3Cl_3$. The alkylaluminoxanes compounds are methyl aluminoxane, ethylaluminoxane, isobutylaluminoxane and modified aluminoxane and volatile removed alkylaluminoxane. The activator c may also be a mixture above, for example, the activator c can be the mixture of TEAL and DMAO, and the molar ratio of TEAL to DMAO is 0.01~100, preferably 0.1~10. The activator c may also be an organic salt activator, such as methyl lithium, methyl magnesium bromide, etc., an inorganic acid and an inorganic salt activator such as tetrafluoroborate ether compound, tetrafluoroborate, hexafluoroantimonate, etc., or an organic boron compound such as cycloboroxane, sodium borohydride, triethylborane, trifluorophenyl boron, tributyl borates and so on.

An ethylene selective oligomerization catalyst system is provided by the embodiment of the present invention. The ligand structure has an important influence on the catalytic activity of ethylene selective oligomerization and the selectivity toward 1-hexene and 1-octene. The transition metal compound (b) is a IVB~VIII group metal compound, and the activator (c) is a compound containing the IIIA group metal. Catalyzed by the catalysts including these ligands, active central metals and activators, the ratios of $C_4$ and $C_{10}$ in the reaction products are very low, and the ratios of $C_6$ and $C_8$ are very high. The carbon number distribution of linear alpha-olefins breaks the S-F distribution, and the high total selectivity toward 1-hexene and 1-octene is achieved.

In another embodiment of the invention, the bridging group A of ligand (a) may be a straight-chain linked group containing Si, such as —$(CH_2)_n$—SiR'R"—$(CH_2)_m$ ($0 \leq n \leq 3$, $0 \leq m \leq 3$), and R' and R" are each independently methyl, isopropyl, cyclohexanyl, cyclopentyl, phenyl, naphthyl, 2,6-diisopropyl phenyl; R and E are as described above.

The transition metal compound b is one of them such as $CrCl_3(THF)_3$, $CoCl_3$, $PbCl_2(COD)$, $Pb(Ac)_2$. And Also can be one of them such as chromium acetate, chromium isooctanate, chromium octanoate, chromium acetylacetone, chromium diisoprene, chromium diphenyl $CrCl_3(THF)_3$, $CrCl_2(THF)_2$, (phenyl) three carbonyl chromium and six carbonyl chromium.

Activator c can be trialkyl aluminum, such as triethyl aluminum, triisobutyl aluminum, tri-n-butyl aluminum, tri-n-hexyl aluminum and tri-n-octyl aluminum, alkyl aluminum halides, alkyl aluminum hydrides or alkyl aluminum hemichlorides, such as $AlEt_2Cl$ and $Al_2Et_3Cl_3$. Alkyl aluminoxane compounds can be selected from methyl aluminoxane, ethyl aluminoxane, isobutyl aluminoxane and modified aluminoxane and volatile removed alkyl aluminoxane. The activator c may also be a mixture of them above, for example, the activator c can be a mixture of TEAL and DMAO, and the molar ratio of TEAL to DMAO is 0.01~100, preferably 0.1~10. The activator c may also be an organic salt activator, such as methyl lithium, methyl magnesium bromide, etc., an inorganic acid and an inorganic salt activator, such as tetrafluoroborate ether compound, tetrafluoroborate, hexafluoroantimonate, etc., and an organic boron compound such as cycloboroxane, sodium borohydride, triethylborane, trifluorophenyl boron, tributyl borates and so on.

The ethylene selective oligomerization catalyst system provided by the embodiment of the invention has a high total selectivity toward 1-hexene and 1-octene, and, in the two components of 1-hexene and 1-octene, the selectivity of one is obviously higher than the other one. High purity 1-hexene or 1-octene can be obtained respectively by simple separation.

The preparation method of the catalyst system is further explained below. Preparation of ligand a:

(1) Preparation of $C_3H_2N_2RLi$, $C_3H_2N_2RLi$ was synthesized by dissolving a certain amount of imidazole with substituents containing N in a suitable volume of tetrahydrofuran and then adding n-butyl lithium in drops at a certain temperature.

(2) Preparation of $C_3H_2N_2R$-A-Cl. Appropriate amount $C_3H_2N_2RLi$ was dissolved in tetrahydrofuran, dichloride of A was dissolved in tetrahydrofuran, and then slowly added into $C_3H_2N_2RLi$ tetrahydrofuran solution in drops at a certain temperature. The solution was stirred overnight at room temperature, then filtered by filter funnel, concentrated in vacuum and crystallized to obtain $C_3H_2N_2R$-A-Cl.

(3) Preparation of $C_3H_2N_2R$-A-E.

Certain amount of $C_3H_2N_2R$-A-Cl was dissolved in n-hexane, and certain amount of lithium salt of E was dissolved in THF. At certain temperature, the latter solution was slowly added to the former solution. After that, the mixture naturally raised to room temperature and was stirred for 2 hours. After filtration by filter funnel, the filtrated cake was the crude $C_3H_2N_2R$-A-E ligand. Ligand a as white or light yellow solid was obtained by recrystallation.

The preparation method of the catalyst system includes the following steps:

The components a, b and c were mixed previously or directly added to the reaction system for in-situ synthesis.

That is to say, the preparation of the catalyst may pre-mix the ligand a, connected by bridging groups containing heteroatoms, transition metal compounds b and activator c. It also can run by directly adding the ligands a, connected by chain alkanes containing heteroatoms, transition metal compounds b and activator c into the reaction system for in-situ synthesis.

The components of ligands a, linked by bridging groups described in general formula I, transition metal compounds b and activator c can be carried out by liquid-phase reactions, for example, under the effect of solvents. The solvents can be toluene, benzene or their derivatives. The reaction can also be carried out by solid-phase reactions. The catalyst also can be formed by in-situ reaction during the oligomerization process. The reaction described herein may be process with one, two or three kinds of the above heteroatom ligands, transition metal compounds and organometallic activators. This reaction is also a aging process (pre-coordination) of the catalyst.

The method for ethylene oligomerization using the above catalyst systems in the presented invention is further explained below.

The embodiment of the invention also provides a method of ethylene oligomerization reaction, including ethylene oligomerization reaction in the presence of the above catalyst system.

In an embodiment of the invention, the reaction was carried out in an inert solvent, which were alkanes, aromatic hydrocarbons, olefins, ionic liquids or their mixture. The typical solvents were, but not limited to, benzene, toluene, xylene, cumene, n-heptane, n-hexane, methylcyclohexane, cyclohexane, 1-hexene, 1-octene, ionic liquids, etc.

In another embodiment of the invention, the reaction temperature was 0° C.~200° C., preferably 50° C.~150° C.

In another embodiment of the invention, the reaction pressure was 0.1 MPa~50 MPa, preferably 1.0 MPa~10 MPa.

In another embodiment of the present invention, the catalyst concentration in the reaction system was 0.01 μmol (metal)/L~1000 μmol(metal)/L, and 0.1 μmol(metal)/L~10 μmol(metal)/L is preferred.

The contents of the present invention are further illustrated by conjunction with specific examples, but they are not limited to the following embodiments.

Example 1

1. Preparation of 1-diphenylphosphonmethyl-3-tert-butyl-imidazole-2-ene ($C_{20}H_{23}N_2P$)

(1) Preparation of 1-tert-butyl-imidazole-3-lithium

THF (200 ml) and 1-tert-butylimidazole (12.42 g, 0.1 mol) were added into a 500 ml reactor containing a stirrer with $N_2$ fully charged. After stirring evenly, the solution was cooled to −45° C. A solution of n-butyl lithium hexane (41.6 ml, 2.4 mol/L) was extracted with a 100 mL syringe and added slowly to the solution above while string. After stirring at −45° C. for 1 hour, the solution was raised to room temperature and kept stirring for 1 hour. Then, the solvent was removed by vacuum, and hexane (100 ml) was added in. 12.08 g (0.098 mol, 92.8%) product was obtained by remove the volatile components in vacuum after dispersion and filtration.

(2) Preparation of Diphenylphosphine Lithium

The dehydrated THF (200 ml) and diphenylphosphine (18.62 g, 0.1 mol) were added to a 500 ml stirred reactor charged by $N_2$ fully, and stirred evenly and then cooled to −80° C. with liquid nitrogen. A solution of n-butyl lithium in hexane (41.6 ml, 2.4 mol/L) was extracted with a 100 ml syringe and added slowly while stirring. After stirring at −80° C. for 1 hour, the solution was raised to room temperature and stirred for 1 hour. Then the solvent was removed by vacuum, and n-hexane (100 ml) was added in. 18.82 g (0.098 mol, 98.6%) product was obtained by remove the volatile components in vacuum after dispersion and filtration.

(3) Preparation of Chloromethyl Diphenyl Phosphine

In a glove box in $N_2$ atmosphere, 150 mL dichloromethane was added to a 250 mL reactor, then cooled to −35° C., and a small amount of diphenylphosphine lithium salt (9.61 g, 0.050 mol) was added to the above solution in batches. After that, the solution was naturally raised to room temperature and then stirred overnight. After filtering, the volatile components were removed by vacuum, and the yellow liquid was obtained. The colorless liquid product 9.97 g (0.042 mol, 85%) was obtained by distillation in vacuum.

(4) Preparation of 1-diphenylphosphine-methyl-3-tert-butyl-imidazole-2-ene

In a glove box in $N_2$ atmosphere, 1-tert-butylimidazole-3-lithium (5.20 g, 0.040 mol) was dispersed in dehydrated n-hexane (100 mL) and cooled to −35° C. Chloromethyl diphenylphosphine (9.97 g, 0.042 mol) was dissolved in 100 mL n-hexane and was added slowly to the above dispersed solution and then naturally raised to room temperature. After stirring overnight, the volatile components were removed by vacuum. The residues were extracted with 50 mL toluene. After filtration, 9.03 g product (0.028 mol, 70%) was obtained by removing the volatile components in vacuum and washed twice with 20 mL n-hexane.

The structures of all ligands were confirmed by nuclear magnetic resonance spectroscopy.

2. Preparation of Catalyst

The dehydrated methylcyclohexane (20 mL), DMAO (methylaluminoxane free of trimethylaluminum) (0.57 g, 9.9 mmol), TEAL (0.38 g, 3.3 mmol), 1-diphenylphosphine-methyl-3-tert-butylimidazole-2-ene (22 mg, 67.8 μmol), $CrCl_3 \cdot (THF)_3$ (12 mg, 33 μmol) were added to a 100 mL stirred reactor with $N_2$ fully charged. The mixture was reacted for 5 min at room temperature to reserve.

3. Ethylene Oligomerization

The 500 mL autoclave was heated to 100° C. and kept in vacuum for 2 hours, then replaced several times with nitrogen and filled with ethylene. After cooling to a predetermined temperature, dehydrated methylcyclohexane (200 mL) and the catalyst were added. The oligomerization reaction was carried out at 45° C. and 1 MPa pressure. After reacting for 30 min, it was terminated with 10% acidified ethanol and cooled by ice bath. Then released the pressure and 41.2 g oligomerization product was obtained. The activity of the catalyst was $2.50 \times 10^6$ g oligomer/mol Cr·h. The distribution of oligomerization products is shown in Table 1.

Example 2

Same as example 1. The difference is that A is —$CH_2CH_2$— group. 44.68 g oligomerization product was obtained, and the activity of the catalyst was $2.71 \times 10^6$ g oligomer/mol Cr·h. The distribution of oligomerization products is shown in Table 1.

Example 3

Same as example 1. The difference is that A is —$CH_2CH_2CH_2$— group, E is diisopropyl phosphino group, and R is methylphenyl. 60.35 g oligomerization product was obtained, and the activity of the catalyst was $3.66 \times 10^6$ g oligomer/mol Cr·h. The distribution of oligomerization products is shown in Table 1.

Example 4

Same as example 1. The difference is that A is —$CH_2Si(CH_3)_2CH_2$— group. 78.3 g oligomerization product was obtained, and the activity of the catalyst was 4.75×10⁶ g oligomer/mol Cr·h. The distribution of oligomerization products is shown in Table 1.

Example 5

Same as example 4. The difference is that R is adamantyl, E is a adamantyl imidazole group which is symmetrical to the left side of A. 74.18 g oligomerization product was obtained, and the activity of the catalyst was 4.50×10⁶ g oligomer/mol Cr·h. The distribution of oligomerization products is shown in Table 1.

Example 6

Same as example 5. The difference is that A is —CH$_2$P (C$_6$H$_5$)CH$_2$— group. 57.19 g oligomerization product was obtained, and the activity of the catalyst was 3.47×10⁶ g oligomer/mol Cr·h. The distribution of oligomerization products is shown in Table 1.

Example 7

Same as example 4. The difference is that E is diphenyl amino group. 22.47 g oligomerization product was obtained, and the activity of the catalyst was 1.36×10⁶ g oligomer/mol Cr·h. The distribution of oligomerization products is shown in Table 1.

Example 8

Same as example 2. The difference is that E is ethyl mercapto group. 62.5 g oligomerization product was obtained, and the activity of the catalyst was 3.79×10⁶ g oligomer/mol Cr·h. The distribution of oligomerization products is shown in Table 1.

Example 9

Same as example 4. The difference is that the pressure is 2 MPa. The oligomerization product 104.33 g was obtained, and the activity of the catalyst was 6.32×10⁶ g oligomer/mol Cr·h. The distribution of oligomerization products is shown in Table 1.

Example 10

Same as example 4. The difference is that the pressure is 4 MPa. The oligomerization product 211.78 g was obtained, and the activity of the catalyst was 1.28×10⁷ g oligomer/mol Cr·h. The distribution of oligomerization products is shown in Table 1.

Example 11

Same as example 4. The difference is that the reaction temperature is 0° C. 27.1 g oligomerization product was obtained, and the activity of the catalyst was 1.64×10⁶ g oligomer/mol Cr·h. The distribution of oligomerization products is shown in Table 1.

Example 12

Same as example 4. The difference is that the reaction temperature is 75° C. 90.1 g oligomerization product was obtained, and the activity of the catalyst was 5.46×10⁶ g oligomer/mol Cr·h. The distribution of oligomerization products is shown in Table 1.

Example 13

Same as example 4. The CrCl$_3$.(THF)$_3$ loading is 3 μmol. 27.7 g oligomerization product was obtained, and the activity of the catalyst was 1.85×10⁷ g oligomer/mol Cr·h. The distribution of oligomerization products is shown in Table 1.

Example 14

Same as example 10. The difference is that MAO is used as cocatalyst. 289.4 g oligomerization product was obtained, and the activity of the catalyst was 1.75×10⁷ g oligomer/mol Cr·h. The distribution of oligomerization products is shown in Table 1.

Example 15

Same as example 10. The difference is that MMAO is used as cocatalyst. 130.1 g oligomerization product was obtained, and the activity of the catalyst was 7.89×10⁶ g oligomer/mol Cr·h. The distribution of oligomerization products is shown in Table 1.

Example 16

Same as example 10. The difference is that the chromium compound is CrCl$_2$(THF)$_2$. 20.9 g oligomerization product was obtained, and the activity of the catalyst was 1.27×10⁶ g oligomer/mol Cr·h. The distribution of oligomerization products is shown in Table 1.

The experimental conditions and catalyst activity of examples 1~16 are shown in Table 2.

TABLE 1

Comparison of carbon number distribution of oligomerization products

| Product distribution | $C_4$ (wt %) | $C_6$ (wt %) | $C_8$ (wt %) | $>C_{10}$ (wt %) | 1-$C_6^-$ [a](wt %) | 1-$C_8^-$ [b](wt %) |
|---|---|---|---|---|---|---|
| Example 1 | 0.13 | 53.22 | 34.28 | 12.37 | 97.43 | 93.61 |
| Example 2 | 0.34 | 47.21 | 39.55 | 12.9 | 96.75 | 94.41 |
| Example 3 | 0.13 | 54.84 | 32.70 | 12.33 | 97.24 | 91.56 |
| Example 4 | 0.23 | 20.66 | 68.34 | 10.77 | 88.87 | 92.74 |
| Example 5 | 0.17 | 25.67 | 64.01 | 10.15 | 89.09 | 96.87 |
| Example 6 | 0.14 | 75.21 | 22.71 | 1.94 | 99.6 | 95.64 |
| Example 7 | 8.33 | 16.78 | 60.71 | 14.18 | 95.2 | 92.54 |
| Example 8 | 5.33 | 45.32 | 39.87 | 9.48 | 94.57 | 91.66 |
| Example 9 | 0.16 | 13.85 | 71.17 | 14.82 | 81.67 | 94.57 |
| Example 10 | 0.21 | 8.78 | 79.65 | 11.36 | 66.21 | 95.17 |
| Example 11 | 0.21 | 7.03 | 86.57 | 6.19 | 60.02 | 96.12 |
| Example 12 | 1.47 | 66.37 | 22.92 | 9.24 | 96.88 | 93.17 |
| Example 13 | 0.33 | 17.54 | 74.67 | 7.46 | 97.54 | 93.67 |
| Example 14 | 22.17 | 25.78 | 19.47 | 32.58 | 97.87 | 98.67 |
| Example 15 | 0.84 | 19.67 | 71.57 | 7.92 | 92.35 | 95.78 |
| Example 16 | 1.02 | 25.37 | 60.75 | 12.68 | 84.67 | 95.37 |

[a] 1-$C_6^-$ in $C_6$.
[b] 1-$C_8^-$ in $C_8$.

TABLE 2 experimental conditions and catalyst activity of embodiments 1~16

| Example | R | A | E | Chromium compound | Reaction temperature °C. | Reaction Pressure MPa | Catalyst concentration mmol Cr/L | a loading μmol | b loading μmol | c loading mmol | Activity $10^6$ g/mol Cr·h |
|---|---|---|---|---|---|---|---|---|---|---|---|
| 1 | tert butyl | —CH$_2$— | diphenylphosphine | CrCl$_3$·(THF)$_3$ | 45 | 1 | 0.16 | 67.8 | 33 | 9.9/3.3 | 2.50 |
| 2 | tert butyl | —CH$_2$CH$_2$— | diphenylphosphine | CrCl$_3$·(THF)$_3$ | 45 | 1 | 0.16 | 67.8 | 33 | 9.9/3.3 | 2.71 |
| 3 | toluene | —CH$_2$CH$_2$CH$_2$— | diisopropylphosphine | CrCl$_3$·(THF)$_3$ | 45 | 1 | 0.16 | 67.8 | 33 | 9.9/3.3 | 3.66 |
| 4 | tert butyl | —CH$_2$Si(CH$_3$)$_2$CH$_2$— | diphenylphosphine | CrCl$_3$·(THF)$_3$ | 45 | 1 | 0.16 | 67.8 | 33 | 9.9/3.3 | 4.75 |
| 5 | adamantyl | —CH$_2$Si(CH$_3$)$_2$CH$_2$— | adamantyl imidazole | CrCl$_3$·(THF)$_3$ | 45 | 1 | 0.16 | 67.8 | 33 | 9.9/3.3 | 4.50 |
| 6 | adamantyl | —CH$_2$P(C$_6$H$_5$)CH$_2$— | adamantyl imidazole | CrCl$_3$·(THF)$_3$ | 45 | 1 | 0.16 | 67.8 | 33 | 9.9/3.3 | 3.47 |
| 7 | tert butyl | —CH$_2$Si(CH$_3$)$_2$CH$_2$— | diphenyl amine | CrCl$_3$·(THF)$_3$ | 45 | 1 | 0.16 | 67.8 | 33 | 9.9/3.3 | 1.36 |
| 8 | tert butyl | —CH$_2$Si(CH$_3$)$_2$CH$_2$— | ethyl mercapto | CrCl$_3$·(THF)$_3$ | 45 | 1 | 0.16 | 67.8 | 33 | 9.9/3.3 | 3.79 |
| 9 | tert butyl | —CH$_2$Si(CH$_3$)$_2$CH$_2$— | diphenylphosphine | CrCl$_3$·(THF)$_3$ | 45 | 2 | 0.16 | 67.8 | 33 | 9.9/3.3 | 6.32 |
| 10 | tert butyl | —CH$_2$Si(CH$_3$)$_2$CH$_2$— | diphenylphosphine | CrCl$_3$·(THF)$_3$ | 45 | 4 | 0.16 | 67.8 | 33 | 9.9/3.3 | 12.78 |
| 11 | tert butyl | —CH$_2$Si(CH$_3$)$_2$CH$_2$— | diphenylphosphine | CrCl$_3$·(THF)$_3$ | 0 | 1 | 0.16 | 67.8 | 33 | 9.9/3.3 | 1.64 |
| 12 | tert butyl | —CH$_2$Si(CH$_3$)$_2$CH$_2$— | diphenylphosphine | CrCl$_3$·(THF)$_3$ | 75 | 1 | 0.16 | 67.8 | 33 | 9.9/3.3 | 5.46 |
| 13 | tert butyl | —CH$_2$Si(CH$_3$)$_2$CH$_2$— | diphenylphosphine | CrCl$_3$·(THF)$_3$ | 45 | 1 | 0.16 | 67.8 | 33 | 9.9/3.3 | 18.50 |
| 14 | tert butyl | —CH$_2$Si(CH$_3$)$_2$CH$_2$— | diphenylphosphine | CrCl$_3$·(THF)$_3$ | 45 | 1 | 0.015 | 67.8 | 33 | MAO 13.2 | 17.52 |
| 15 | tert butyl | —CH$_2$Si(CH$_3$)$_2$CH$_2$— | diphenylphosphine | CrCl$_3$·(THF)$_3$ | 45 | 1 | 0.16 | 67.8 | 33 | MMAO 13.2 | 7.89 |
| 16 | tert butyl | —CH$_2$Si(CH$_3$)$_2$CH$_2$— | diphenylphosphine | CrCl$_2$·(THF)$_2$ | 45 | 1 | 0.16 | 67.8 | 33 | 9.9/3.3 | 1.27 |

What is claimed is:

1. A catalyst for selective oligomerization of ethylene, comprising three components:
a ligand, wherein the ligand comprises carbene groups of imidazole ring;
a transition metal compound, wherein the transition metal compound contains chromium; and
an activator, wherein the activator is a mixture of alkyl aluminum compound and alkyl aluminoxane compound removed of volatile components, in which the alkyl aluminum compound is triethyl aluminum and the alkyl aluminoxane compound is methyl aluminoxane removed of volatile components;
wherein the ligand contains at least one group as shown in general formula I as shown below;

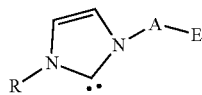

I wherein the main chain of the bridging group A is —(CH$_2$)$_n$—SiR'R"—(CH$_2$)$_m$ (0≤n≤3, 0≤m≤3), in which R' and R" are each independently methyl, isopropyl, cyclohexanyl, cyclopentyl, phenyl, naphthyl or 2,6-diisopropyl phenyl, respectively;
the group E is a linear or cyclic group containing a second heteroatom, and the group E is selected from the group consisting of diisopropyl phosphino, dicyclohexyl phosphino, dimethyl phosphino, diethyl phosphino, diphenyl phosphino, di-o-methylbenzene phosphino, di-o-ethylphenyl phosphino, di-o-isopropylphenyl phosphino, diphenyl phosphino, dinaphthyl phosphino, methoxy, ethoxy, phenoxy, isopropoxy, methyl mercapto, ethyl mercapto, phenylmercapto, and isopropyl Mercapto;
R is a hydrocarbyl group.

2. The catalyst according to claim 1, wherein R in general formula I is selected from the group consisting of an alkyl group, a vinyl group, and an aromatic group.

3. The catalyst according to claim 1, wherein a molar ratio of the triethyl aluminum to the methyl aluminoxane removed of volatile components is 0.01-100.

4. The catalyst according to claim 1, wherein a molar ratio of ligand, the transition metal compound and the activator is 1:(0.5-100):(0.1-5000).

5. A method for an ethylene oligomerization reaction by carrying out the ethylene oligomerization reaction in the presence of the catalyst according to claim 1, comprising mixing ethylene with the catalyst.

* * * * *